United States Patent

Blaha et al.

[11] Patent Number: 5,342,351
[45] Date of Patent: Aug. 30, 1994

[54] BEAM POSITIONING DEVICE FOR AN OPHTHALMOLOGICAL INSTRUMENT

[75] Inventors: Erich Blaha, Essingen; Martin Poxleitner, Konigsbronn; Gerhard Hanemann, Oberkochen, all of Fed. Rep. of Germany

[73] Assignee: Carl Zeiss-Stiftung, Heidenheim, Fed. Rep. of Germany

[21] Appl. No.: 102,086

[22] Filed: Aug. 4, 1993

[30] Foreign Application Priority Data

Aug. 19, 1992 [DE] Fed. Rep. of Germany ....... 4227390

[51] Int. Cl.⁵ .................................. A61B 17/36
[52] U.S. Cl. ............................. 606/4; 606/5; 606/11
[58] Field of Search ................. 606/4, 5, 6, 10, 11

[56] References Cited

U.S. PATENT DOCUMENTS 4,409,979 10/1983 Roussel et al. ................. 606/4
4,776,335 10/1988 Nakanishi et al. ............. 606/17
5,226,903 7/1993 Mizuno ........................... 606/4

Primary Examiner—Stephen C. Pellegrino
Assistant Examiner—Sonya Harris

[57] ABSTRACT

For defined positioning of a laser beam in an ophthalmological instrument with a slit projection device and an optical observation unit, a focusing objective is displaced by a displacement device in a plane parallel to the observation beam path of the optical observation unit. The laser beam path and the slit projection beam path are separately deflected coaxially with the observation beam path in the direction of the target plane. Defined positioning of a laser beam in the patient's eye is achieved by means of the displacement device, which includes a displacement element connected to the focusing objective, and an operating element. The displacement device furthermore offers diverse means of adjustment.

16 Claims, 3 Drawing Sheets

BEAM POSITIONING DEVICE FOR AN OPHTHALMOLOGICAL INSTRUMENT

BACKGROUND OF THE INVENTION

1. Field of the Invention

The invention relates to a beam positioning device for an ophthalmological instrument.

2. Description of the Prior Art

So-called laser slit lamps are known for treating retinal damage. In laser slit lamps, a treatment laser beam is coupled in between the two observation beam paths. To precisely position the laser beam on the retina, it is usual to couple in the laser beam via a deflecting element, e.g., a mirror or a prism. A micro manipulator is used to adjust the deflecting element in its angular position relative to the optical axis. Such an apparatus is described, for example, in U.S. Pat. No. 5,002,386 and U.S. Pat. No. 5,067,951. Coupling the deflections of the deflecting element and a deflecting prism with a cemented-on focusing element allows defined positioning of the laser beam. This arrangement is an expensive mechanism for ensuring a defined positioning of the laser beam on the retina.

A further possibility for positioning the laser beam on the retina is known from U.S. Pat. No. 4,776,336, which is commonly owned with the present invention. First, the treatment laser beam is coupled into the slit projection beam path via a first deflecting element. Then the coaxial laser beam path and slit projection beam path are coaxially united with the beam path of a further target laser via a second deflecting element. Positioning the point where the treatment laser is incident on the retina is brought about by defined displacement of an optical focusing element in a horizontal plane. This optical focusing element is arranged between the first and second deflecting elements. When the optical focusing element is displaced, the slit to be imaged and the point of incidence of the laser beam on the retina are simultaneously displaced in the eye. This is undesirable in various kinds of investigations. Furthermore, an arrangement of this kind is not suitable for retrofitting a conventional slit lamp with a corresponding laser attachment. Another combination of an ophthalmological instrument and a laser photocoagulator is described in U.S. Pat. No. 3,703,176. In that patent, the laser beam is positioned on the retina by laterally displacing a lens in the laser beam path. After passing through this lens the laser beam passes through a small hole in a deflecting mirror and is then coaxially aligned with the slit lamp illuminating light, which is deflected by the deflecting mirror in the same direction as the laser beam. The laser beam and the slit lamp illumating light are focused by one common lens, which is arranged between the deflecting mirror with the hole and a prism, which deflects both beams to the patient's eye.

This arrangement has several disadvantages. First, the positioning of the laser beam on the retina is limited by the dimension of the hole in the deflecting mirror. If the laser beam is laterally displaced by a greater amount, only a part of the entire laser beam diameter is available for photocoagulation on the retina. Second, if the hole in the deflecting mirror is enlarged to avoid this problem, the slit lamp illuminating light decreases. Thus, this arrangement does not position the laser beam on the retina in a satisfactory manner.

SUMMARY OF THE INVENTION

The object of the invention is to provide a beam positioning device for ophthamological instruments that has the simplest possible structure and can be used for retrofitting ophthamological instruments. In particular, positioning of a slit and a laser beam in a target plane are to be independent of each other. Simple and reliable handling of such a beam positioning device is also desirable.

These objects are achieved in the present invention by a beam positioning device having:

a radiation source beam path including a radiation source, at least one optical means for beam dimensioning or focusing and first deflecting means for deflecting the radiation source beam path into the target plan. The beam positioning device also has optical observation means including at least one observation beam path for viewing the target plane, a slit projection beam path, including a plurality of optical elements and second deflection means for deflecting the slit projection beam path into the target plane. Displacement means define displacement of at least one of the optical means in the radiation source beam path relative to the first deflecting means perpendicularly to the radiation source beam path, without affecting the slit projection beam path.

The present invention offers advantages over the cited prior art. First, in contrast to the cited prior art, positioning of a laser beam in the target plane takes place by means of a displacement device, which makes possible solely a defined displacement of at least one optical element (preferably the focusing objective) in the radiation source beam path. Due to these features, expensive mechanical coupling between the deflection motions of the deflecting element and the focusing element, as in U.S. Pat. No. 5,002,386 mentioned above, is thereby avoided. Second, in contrast to U.S. Pat. No. 4,765,336, independent positioning of the slit image in the target plane is possible. Furthermore, a simple retrofitting of opthalmological instruments (for example, conventional slit lamps) with a laser attachment is made possible by the orientation of the observation, treatment, and slit projection beam paths according to the invention.

Advantageously, the optical observation unit is a stereo microscope with two observation beam paths in a horizontal plane.

Preferably, the deflecting elements for deflecting the slit projection beam paths and the radiation source beam path to the target plane are arranged centrally between the observation beam paths. The deflecting elements for the slit projection beam path make possible coaxial coupling-in of the radiation source beam path. The slit projection beam path is made up of two partial beam bundles. The partial beam bundles are deflected in the direction of the target plane by a two-part deflecting element. Differing path lengths are caused by the two-part deflecting elements over which the partial beam bundles pass. Optical elements are provided in the slit projection beam path to compensate for these differing optical path lengths.

In a preferred embodiment, the displacement device for defined positioning of the focusing objective includes an operating element. This operating element allows the user to effect a desired deflection of the laser beam path in a target plane. The focusing objective in the radiation source beam path is connected to a displacement element of the displacement device. The displacement element is mounted to be suitably movable. The displacement element can be positioned in a defined manner in a plane oriented perpendicularly to the radiation source beam path by means of the operating element. In an advantageous embodiment, an adjusting unit is arranged in the displacement device. The adjusting unit makes possible a defined adjustment of a null position of the displacement element. This, in turn allows the incidence point of the laser beam to be correspondingly fixed in the target plane. The adjusting unit is movable relative to the displacement element within certain tolerances. The adjusting unit can be fixed in a desired position by means of fasteners. Furthermore, it is possible to provide elastic elements within the adjusting unit that ensure an automatic return of the displacement element to a defined null position after displacement. The elastic elements exert a force on the displacement element that can be adjusted in a defined manner by means of adjusting elements. Accordingly, the exerted force can be fully removed from the displacement element and automatic return into a defined null position can be thereby selectively canceled. One or more arresting elements can be arranged within the displacement device. These arresting elements make it possible to fix the displacement device in a set position and prevent an inadvertent displacement of the laser beam in the target plane.

In an advantageous embodiment, the displacement element has a longitudinal guide that moves about a suitably positioned pivot point fixed to the ophthamological instrument. This arrangement ensures that the incidence point of the laser beam is displaced to the correct side in the target plane during corresponding movement of the operating element by the user.

BRIEF DESCRIPTION OF THE DRAWINGS

Further advantages and details of the beam positioning device according to the invention will now be described, with reference to the drawings, in which.

DETAILED DESCRIPTION OF PREFERRED EMBODIMENTS

Figure 1:
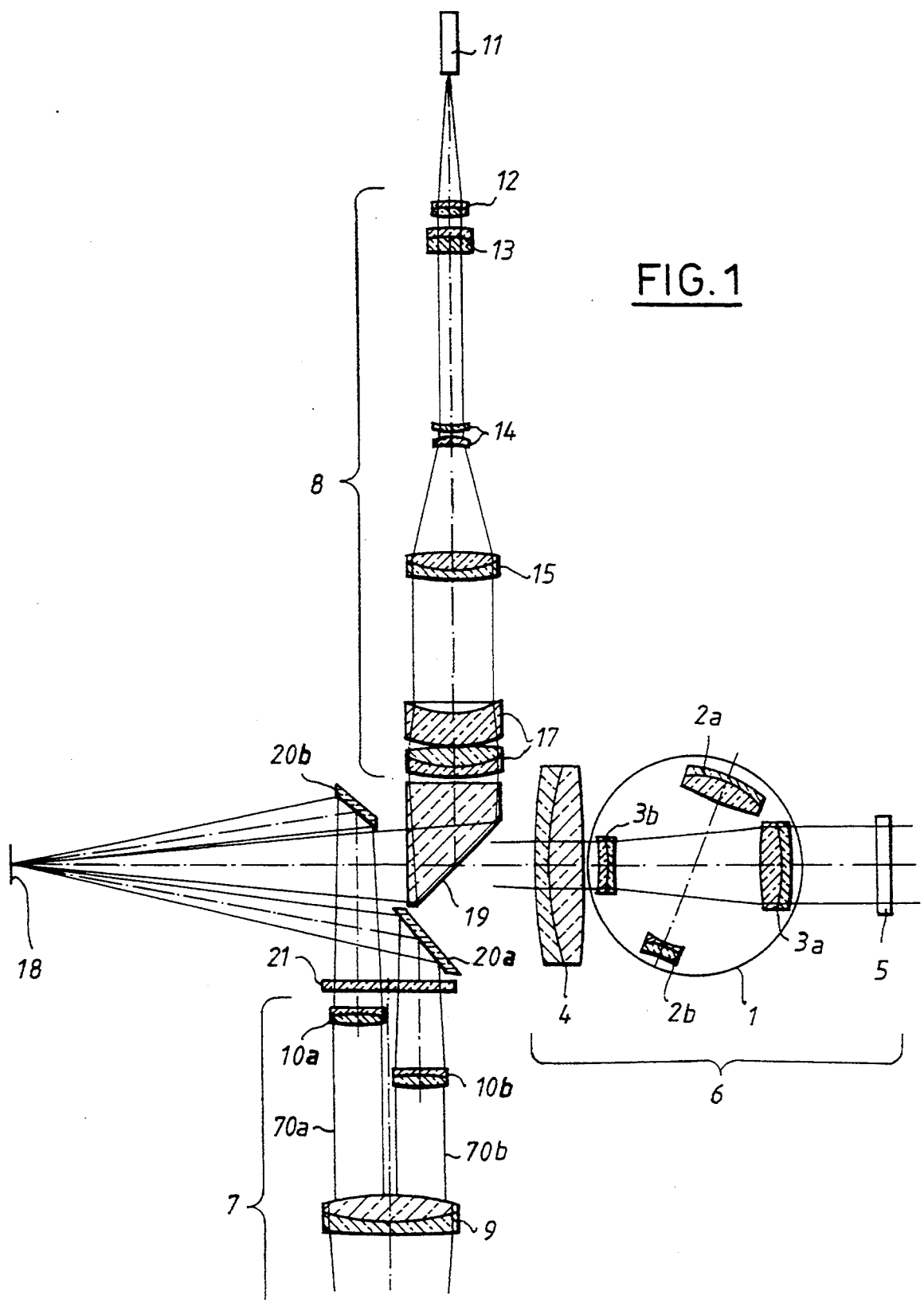
FIG. 1 shows a schematic sectional representation of the optical structure of the beam positioning device.

The principal optical structure of the beam positioning device according to the invention is described with reference to FIG. 1. In the embodiment shown, a stereo microscope has two observation beam paths (6) arranged in a horizontal plane. Only one observation beam path is visible in this side view. The following important elements of the stereo microscope are shown: a main objective (4), a device (1) for changing the enlargement, and a protective filter (5) that protects the observer from possibly damaging reflected rays. According to the treatment wavelength used, this protective filter can either be permanently fixed, or pivoted in by a motor drive. The device for changing the enlargement (1) includes optical systems (2a, 2b; 3a, 3b), having different enlargements that can be selectively pivoted in. The protective filter is followed by a conventional binocular tube (not shown).

A slit projection beam path (7) is perpendicularly oriented to the observation beam path (6). The slit projection beam path includes a light source (not shown) with a slit diaphragm (not shown) arranged in front of the light source, and subsequent optical elements for projection of the slit diaphragm in the target plane (18). Of these optical elements, only a first achromat (9); additional achromats (10a, 10b); and a glass cover (21) are shown. Devices can be used for slit diaphragm projection that permit the slit to be selectively projected in various shapes and sizes. Functions and advantages of equal focal length achromats (10a, 10b) in the slit projection beam path (7) will be explained later in the description.

A radiation source beam path (8) is perpendicularly oriented to the two observation beam paths (6), and in the opposite direction to the slit projection beam path (7). Radiation of a laser (not shown) is coupled into an optical system via an optical wave guide (11) and an exit lens (12). The optical system consists of several optical elements for dimensioning and focusing the radiation beam in a target plane (18). This optical system includes diverse optical elements such as a conventional Gallileon beam widener (13, 14, 15) for dimensioning the beam diameter in the target plane (18), and a two-part focusing objective (17) for focusing the beam in the target plane (18). A first deflecting element (19), for example a mirror or a prism, is fixedly mounted to the instrument. The first deflecting element deflects the radiation source beam path (8) in the direction of the observation beam paths (6), i.e. in the direction of the target plane (18). The deflection of the slit projection beam path (7) in the direction of the target plane (18) takes place by means of a second deflecting element (20a, 20b).

In the embodiment shown, the deflection of the slit projection beam path (7) in the direction of the observation beam propagation takes place only after the deflection of the radiation source beam path (8). The second deflecting element (20a, 20b) consists of two individual mirrors. The radiation source beam path (8) is coupled-in between these mirrors. The slit projection beam path (7) includes partial beam bundles (70a, 70b) that are deflected by the two individual mirrors of the second deflecting element (20a, 20b) in the direction of the target plane (18). Thus, these partial beam bundles (70a, 70b) have different optical path lengths, i.e., the focal points of the partial beam bundles (70a, 70b) do not both lie in the target plane (18) without suitable corrective measures. The different optical path lengths of the partial beam bundles (70a, 70b) are compensated by corresponding positioning of the achromats of equal focal length (10a, 10b) in the slit projection beam path, so that the focal points of both partial beam bundles (70a, 70b) lie in the target plane (18).

For defined positioning of the laser beam in the target plane (18), the optical axis of the radiation source beam path (8) must be at least partially displaced relative to the first deflecting element (19). In this case, the displacement is perpendicular to the radiation source beam path, i.e., in a plane parallel to the plane of the observation beam paths (6) (a horizontal plane perpendicular to the plane of the drawing). For this purpose, the focusing objective (17) is preferably displaced. A suitable displacement device will be further described with reference to FIGS. 2 and 3.

Figure 2:
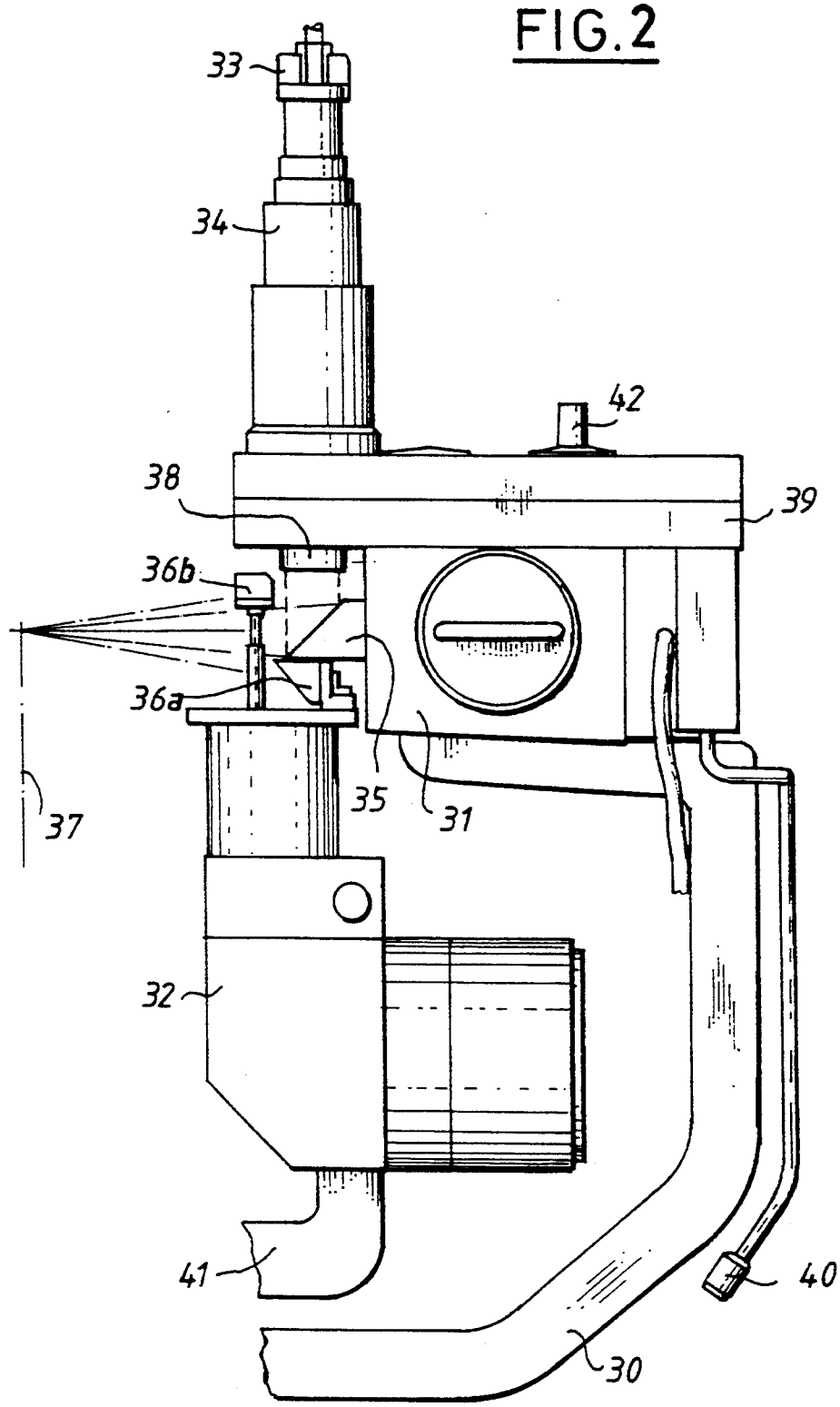
FIG. 2 shows a side view of a first preferred embodiment, with the beam positioning device integrated in a laser slit lamp.

FIG. 2 is a side view of the first embodiment. It shows the beam positioning device according to the invention in connection with a slit projection device (32) and a stereo microscope (31). A stereo microscope (31) is arranged on a support arm (30). Only the microscope body, without the binocular tube, can be seen in this drawing. The two observation beam paths define a horizontal plane that is perpendicularly oriented to the plane of the drawing. The slit projection device (32) is arranged on a second support arm (41) in front of the support arm (30), with the corresponding optical elements arranged as shown in FIG. 1. The slit projection beam path is oriented perpendicularly to the two observation beam paths, and can be pivoted about an axis relative to the target plane (37) in the usual manner. Opposite the slit projection beam path is the radiation source beam path, defined by optical elements (not shown) following an optical wave guide (33) located in an attachment portion (34) on the stereo microscope (31). Preferably, the radiation of a laser (not shown), for example an argon laser, is coupled into the optical wave guide (33).

The radiation source beam path and the slit projection beam path are deflected into the plane of the two observation beam paths in the direction of the target plane (37) by two deflecting elements (35, 36a, 36b). The two deflecting elements (35, 36a, 36b) are arranged in the center between the two observation beam paths of the stereo microscope (31). Special attention should be paid to how far the deflecting elements extend in the direction of the stereo base. To avoid unacceptable vignetting in the observation beam paths, this should not become too large. The deflecting element (35) for the radiation source beam path is a fixed mirror. The fixed mirror is arranged at a 45° angle in relation to the optical axis of the radiation source beam path and the observation beam paths. Consequently, a 90° deflection of the laser beam takes place in the direction of the target plane (37). Alternatively, a suitable prism can be used instead of the fixed mirror. The slit projection device (32) is followed by a fixed second deflecting element (36a, 36b) in the direction of the beam propagation. The second deflecting element consists of two individual mirrors that effect a 90° deflection of the slit projection beam path in the direction of the target plane (37). The second deflecting element (36a, 36b) is constructed in two parts as two individual mirrors (36a, 36b), to enable coaxial coupling-in of the laser beam path. The radiation source beam path is coupled in between the two individual mirrors (36a, 36b).

In the embodiment shown, the displacement device displaces the focusing objective (38) perpendicularly to the radiation source beam path, in a plane parallel to the observation beam paths. The displacement device includes a movably mounted displacement element and an adjusting unit (under cover in this drawing). The operating element (40) of the displacement device enables sensitive positioning of the displacement element in a horizontal plane. By displacing the displacement element or the focusing objective (38) connected to it in this horizontal plane, displacement of the radiation source beam path is effected in the target plane (37), which is perpendicular to this horizontal plane. The operating element (40) is not centrally arranged between the two observation beam paths in the embodiment shown. Rather, it extends laterally downwards past the microscope body (31). An arresting element (42) can also be seen in FIG. 2. The arresting element (42) fixes the movably mounted displacement element of the displacement device in a set position. Once set, this arresting element prevents inadvertent displacement out of this position. Further details regarding the displacement device will be described with reference to the second embodiment shown in FIG. 3.

Figure 3:
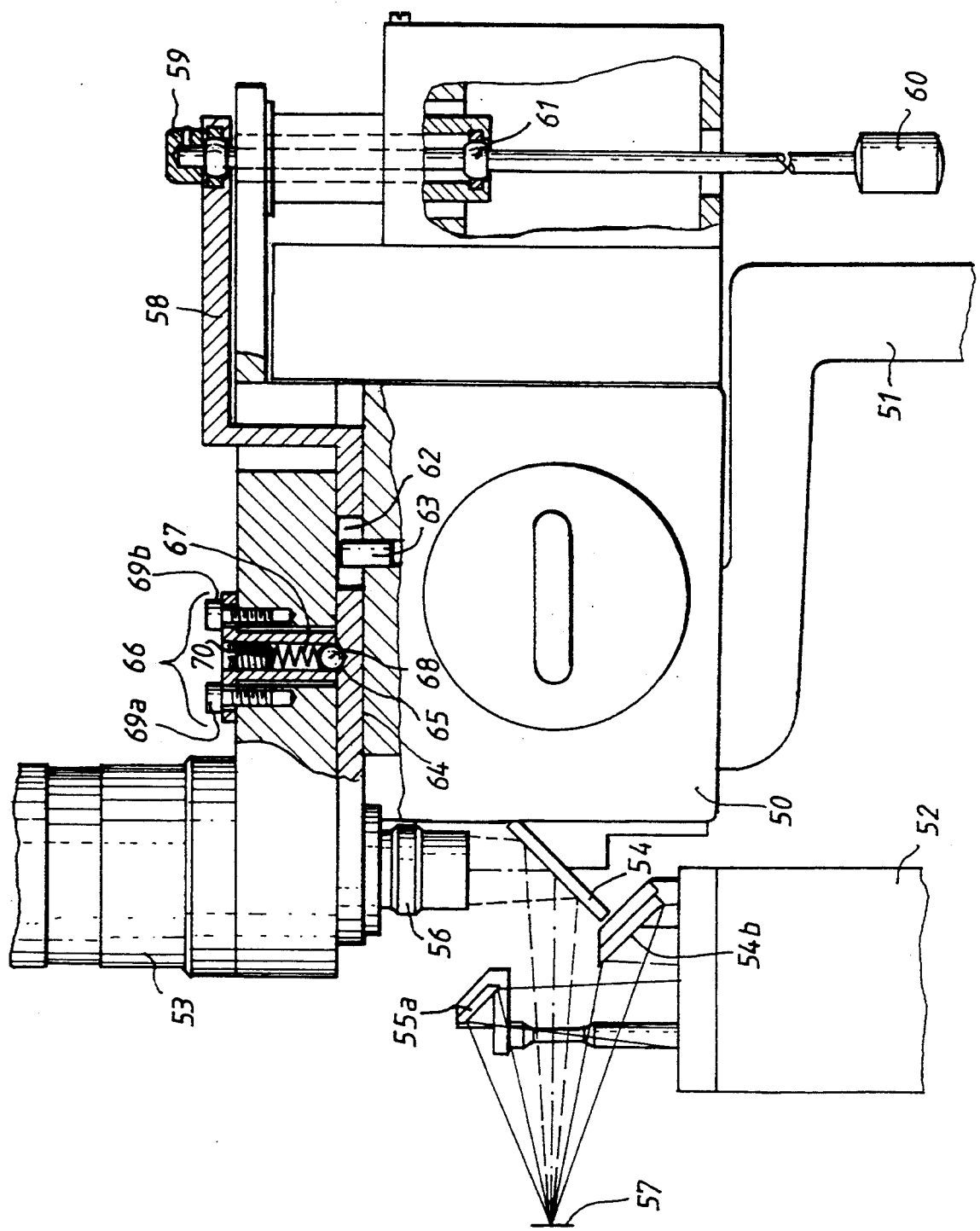
FIG. 3 shows a lateral, partially sectional representation of a second preferred embodiment of the beam positioning device integrated in a laser slit lamp.

FIG. 3 is a partial sectional view of a second embodiment of the device according to the invention. It will be described in detail, particularly with regard to the displacement device for displacing the focusing objective (56). In the embodiment illustrated, displacement of the focusing objective takes place perpendicularly to the radiation source beam path in a horizontal plane that is oriented parallel to the observation beam paths. A stereo microscope (50) is arranged on a corresponding support arm (51), with the microscope observation beam paths defining a horizontal plane. Respectively opposed perpendicularly to this plane are a slit projection device (52) and an attachment (53) for coupling in a radiation source beam path. A laser again serves as a suitable radiation source. The laser's radiation is coupled in via an optical wave guide (not shown) in the attachment (53) together with optical elements for beam dimensioning and focusing. As in the embodiment of FIG. 2, the radiation source beam path and the slit projection beam path are deflected by means of two deflecting elements (54, 55a, 55b). The deflecting element for the slit projection beam path is again embodied in two parts, to facilitate coaxial coupling in of the laser beam path. In order to horizontally displace the focusing objective (56) and effect a defined positioning of the laser beam in the target plane (57), the focusing objective (56) is firmly connected to a displacement element (58). This displacement element (58) is movably mounted in one or more bearings (59), which are preferably Cardan bearings. An operating element (60) is connected to the displacement element (58) by means of bearing (59) and in this embodiment extends downwards centrally between the two observation beam paths. Moving the operating element (60) mounted in another, preferably Cardan, bearing (61), displaces the displacement element (58) and the focusing objective (56) in a horizontal plane.

An elongate guide (62) is oriented in the observation direction in the displacement element (58). A pin (63) is connected to the microscope body and projects into the elongate guide (62), to guide the displacement element (58) on support surface (64). The support surface is securely fixed on the instrument. Pin (63), which guides displacement of the displacement element (58) in a plane, also serves as a pivot point for the force acting via the operating element (60). This arrangement ensures that the point of incidence of the laser beam is displaced to the correct side in the target plane (57) during corresponding movement of the operating element (60). The pin (63) thus permits displacement of the displacement element (58) or the focusing objective (56) in the direction of the target plane (57) and back, and also revolution of the displacement element (58) or the focusing objective (56) about the pin (63) in the plane.

The support surface (64) for the deflecting element (58), which is securely fixed on the instrument, has a trough-like recess. Into this recess, a small ball (68) is pressed by a spring (67) in an adjusting unit (66). The adjusting unit (66) is horizontally movable relative to the microscope body (50) within a certain tolerance. The adjusting unit can be fixed in a desired position relative to the deflecting element (58) by means of adjusting screws (69a, 69b). Since the spring (67) presses downwards on the ball (68), a desired null position of the displacement element (58), i.e., the incidence point of the laser beam in the target plane (57), is adjustable and reproducible. After displacement out of this null position, the displacement element (58) is forced back again into this null position, i.e., the deepest point of the trough-shaped depression (65). The adjusting screw (70) presses on the spring (67) and allows the spring to exert force on the ball (68). If return into a certain null position is not desired, the spring (67) can be fully unloaded, so that no automatic return to a null position results. The spring's force on the ball can be adjusted in a defined manner, by means of the adjusting screw (70), which presses on the spring (67). Adjusting the spring force on the ball (68) by means of the adjusting screw (70) can also adjust the force required for the operating element (60).

We claim:

1. A laser beam positioning device for an ophthalmological instrument having a target plane, comprising
a radiation source for producing a laser beam,
first optical means for focusing or dimensioning said laser beam,
deflecting means for deflecting said laser beam into said target plane,
optical observation means defining at least one observation beam path for viewing said target plane,
second optical means defining a slit projection beam path for focusing a slit into said target plane, and
displacement means for defined displacement of at least one of said first optical means relative to said deflecting means perpendicularly to said laser beam,
said displacement means comprising adjustment means for adjusting the force required to operate said displacement means.

2. A laser beam positioning device according to claim 1, wherein said adjustment means comprises means for precise adjustment of said laser beam in said target plane.

3. A laser beam positioning device according to claim 2, wherein said adjustment means comprises means for adjusting a reproducible null position of said displacement means.

4. A laser beam positioning device according to claim 3, wherein said displacement means further comprises a displacement element connected to said at least one first optical means, said adjustment means is moveable within defined limits relative to said displacement element, and said adjustment means further comprises fixing means for securing said adjustment means in a desired position within said defined limits relative to said displacement element.

5. A laser beam positioning device according to claim 3, wherein said displacement means further comprises a displacement element connected to said at least one first optical means, and said adjustment means further comprises at least one elastic means for facilitating automatic return of said displacement element into said reproducible null position following movement of said displacement element.

6. A laser beam positioning device according to claim 5, wherein said elastic means exerts a force on said displacement element, and said adjustment means further comprises at least one adjusting element acting on said elastic means for adjusting said force exerted by said elastic means.

7. A laser beam positioning device according to claim 1, wherein said displacement means further comprises a displacement element connected to said at least one first optical means and arresting means for fixing the position of said displacement element.

8. A laser beam positioning device according to claim 1, wherein said displacement means comprises a displacement element connected to said at least one optical means, at least one bearing means movably mounted to said displacement element and operating means connected to said bearing means for defined positioning of said displacement element in a horizontal plane.

9. A laser beam positioning device according to claim 8, wherein said at least one optical means comprises a focusing objective through which said laser beam passes.

10. A laser beam positioning device according to claim 8, further comprising longitudinal guide means on said displacement element and fixed pivot means cooperating with said longitudinal guide means to facilitate relative motion of said displacement means in a horizontal plane about said fixed pivot means.

11. A laser beam positioning device according to claim 1, wherein said optical observation means comprises a stereo microscope defining two observation beams oriented in a horizontal plane.

12. A laser beam positioning device according to claim 11, wherein said deflecting means for deflecting said laser beam comprises fixed mirror means arranged between said observation beam path(s) and oriented at an angle of 45 degrees to said observation beam path(s) and at an angle of 45 degrees to said laser beam.

13. A laser beam positioning device for an ophthalmological instrument having a target plane, comprising
a radiation source for producing a laser beam,
first optical means for focusing or dimensioning said laser beam,
deflecting means for deflecting said laser beam into said target plane,
optical observation means defining at least one observation beam path for viewing said target plane,
second optical means defining a slit projection beam path for focusing a slit into said target plane, and
displacement means for defined displacement of at least one of said first optical means relative to said deflecting means perpendicularly to said laser beam,
said displacement means comprising adjustment means for adjusting a reproducible null position of said displacement means.

14. A laser beam positioning device according to claim 13, wherein said displacement means further comprises a displacement element connected to said at least one first optical means, and said adjustment means comprises at least one elastic means for facilitating automatic return of said displacement element into said reproducible null position following movement of said displacement element.

15. A laser beam positioning device according to claim 14, wherein said elastic means exerts a force on said displacement element, and said adjustment means further comprises at least one adjusting element acting on said elastic means for adjusting said force exerted by said elastic means.

16. A laser beam positioning device for an ophthalmological instrument having a target plane, comprising
a radiation source for producing a laser beam, first optical means for focusing or dimensioning said laser beam, deflecting means for deflecting said laser beam into said target plane, optical observation means defining at least one observation beam path for viewing said target plane, second optical means defining a slit projection beam path for focusing a slit into said target plane, displacement means for defined displacement of at least one of said first optical means relative to said deflecting means perpendicularly to said laser beam, said displacement means comprising a displacement element connected to at least one of said first optical means, at least one bearing means movably mounted to said displacement element, an operating means connected to said bearing means for defined positioning of said displacement element in a horizontal plane and adjustment means for precise adjustment of said first optical means, said adjustment means comprising means for adjustment of a reproducible null position of said displacement element.

* * * * *